(12) United States Patent
Zhang et al.

(10) Patent No.: US 7,993,280 B2
(45) Date of Patent: *Aug. 9, 2011

(54) RAPID SHALLOW BREATHING DETECTION FOR USE IN CONGESTIVE HEART FAILURE STATUS DETERMINATION

(75) Inventors: Yi Zhang, Plymouth, MN (US); John D. Hatlestad, Maplewood, MN (US); Yousufali H. Dalal, Irvine, CA (US); Marina Brockway, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/847,645

(22) Filed: Jul. 30, 2010

(65) Prior Publication Data
US 2010/0298732 A1    Nov. 25, 2010

Related U.S. Application Data

(63) Continuation of application No. 11/229,316, filed on Sep. 16, 2005, now Pat. No. 7,775,983.

(51) Int. Cl.
*A61B 5/08*    (2006.01)
(52) U.S. Cl. .................................. 600/529; 600/484
(58) Field of Classification Search ........... 600/529–543
See application file for complete search history.

(56) References Cited

U.S. PATENT DOCUMENTS

| 4,697,591 A | 10/1987 | Lekholm et al. |
| 5,063,927 A | 11/1991 | Webb et al. |
| 5,133,353 A | 7/1992 | Hauser |
| 5,179,945 A | 1/1993 | Van Hofwegen et al. |
| 5,314,459 A | 5/1994 | Swanson et al. |
| 5,318,597 A | 6/1994 | Hauck et al. |
| 5,372,606 A | 12/1994 | Lang et al. |
| 5,411,525 A | 5/1995 | Swanson et al. |
| 5,468,254 A | 11/1995 | Hahn et al. |
| 5,593,431 A | 1/1997 | Sheldon |
| 5,620,466 A | 4/1997 | Haefner et al. |
| 5,634,938 A | 6/1997 | Swanson et al. |
| 5,662,688 A | 9/1997 | Haefner et al. |

(Continued)

FOREIGN PATENT DOCUMENTS
EP    1151719    7/2001
(Continued)

OTHER PUBLICATIONS

Altshule et al., "The Effect of Position on Periodic Breathing in Chronic Cardiac Decomposition", New Eng. Journal of Med., vol. 259, No. 22, pp. 1064-1066, Nov. 27, 1958.

(Continued)

*Primary Examiner* — Charles A Marmor, II
*Assistant Examiner* — Karen E Toth
(74) *Attorney, Agent, or Firm* — Hollingsworth & Funk, LLC

(57) ABSTRACT

Systems and methods involve use of a medical device comprising sensing circuitry. One or more respiratory parameters are detected using the device. Patient baseline weight is provided, and an output signal indicative of a patient's congestive heart failure status is generated based on a change in the one or more respiratory parameters and a change in the patient's measured weight or predicted weight relative to the patient baseline weight. The respiratory parameters may include one or more of respiration rate, relative tidal volume, an index indicative of rapid shallow breathing by the patient, an index derived by computing a respiration rate and a tidal volume for each patient breath, and an index indicative of dyspnea, for example.

24 Claims, 13 Drawing Sheets

U.S. PATENT DOCUMENTS

| | | | | |
|---|---|---|---|---|
| 5,697,953 | A | 12/1997 | Kroll et al. | |
| 5,957,861 | A | 9/1999 | Combs et al. | |
| 5,967,981 | A * | 10/1999 | Watrous | 600/428 |
| 5,974,349 | A | 10/1999 | Levine | |
| 6,044,297 | A | 3/2000 | Sheldon et al. | |
| 6,083,173 | A * | 7/2000 | Grant et al. | 600/529 |
| 6,275,727 | B1 | 8/2001 | Hopper et al. | |
| 6,360,127 | B1 | 3/2002 | Ding et al. | |
| 6,409,675 | B1 | 6/2002 | Turcott | |
| 6,438,407 | B1 | 8/2002 | Ousdigian et al. | |
| 6,449,509 | B1 | 9/2002 | Park et al. | |
| 6,454,719 | B1 | 9/2002 | Greenhut | |
| 6,513,532 | B2 | 2/2003 | Mault et al. | |
| 6,527,729 | B1 | 3/2003 | Turcott | |
| 6,564,106 | B2 | 5/2003 | Guck et al. | |
| 6,572,557 | B2 | 6/2003 | Tchou et al. | |
| 6,658,292 | B2 | 12/2003 | Kroll et al. | |
| 6,666,826 | B2 | 12/2003 | Salo et al. | |
| 6,705,990 | B1 | 3/2004 | Gallant et al. | |
| 6,708,058 | B2 | 3/2004 | Kim et al. | |
| 6,741,885 | B1 | 5/2004 | Park et al. | |
| 6,752,765 | B1 | 6/2004 | Jensen et al. | |
| 6,832,113 | B2 | 12/2004 | Belalcazar | |
| 6,856,829 | B2 | 2/2005 | Ohsaki et al. | |
| 6,922,587 | B2 | 7/2005 | Weinberg | |
| 6,993,389 | B2 | 1/2006 | Ding | |
| 7,013,176 | B2 | 3/2006 | Ding | |
| 7,020,521 | B1 | 3/2006 | Brewer et al. | |
| 7,041,061 | B2 | 5/2006 | Kramer | |
| 7,115,096 | B2 | 10/2006 | Siejko | |
| 7,158,830 | B2 | 1/2007 | Yu | |
| 7,181,285 | B2 | 2/2007 | Lindh | |
| 7,206,634 | B2 | 4/2007 | Ding | |
| 7,228,174 | B2 | 6/2007 | Burnes | |
| 7,306,564 | B2 | 12/2007 | Nakatani et al. | |
| 7,310,554 | B2 | 12/2007 | Kramer | |
| 7,343,199 | B2 | 3/2008 | Hatlestad | |
| 7,376,457 | B2 | 5/2008 | Ross | |
| 7,389,141 | B2 | 6/2008 | Hall | |
| 7,409,244 | B2 | 8/2008 | Salo | |
| 7,468,032 | B2 | 12/2008 | Stahmann et al. | |
| 7,483,743 | B2 | 1/2009 | Mann et al. | |
| 7,572,225 | B2 | 8/2009 | Stahmann et al. | |
| 2001/0037067 | A1 | 11/2001 | Tchou et al. | |
| 2001/0049470 | A1 * | 12/2001 | Mault et al. | 600/300 |
| 2002/0143264 | A1 | 10/2002 | Ding et al. | |
| 2003/0055461 | A1 * | 3/2003 | Girouard et al. | 607/17 |
| 2004/0116819 | A1 | 6/2004 | Alt | |
| 2004/0122294 | A1 | 6/2004 | Hatlestad et al. | |
| 2004/0127792 | A1 | 7/2004 | Siejko | |
| 2004/0133079 | A1 | 7/2004 | Mazar et al. | |
| 2005/0137629 | A1 | 6/2005 | Dyjach et al. | |
| 2006/0020295 | A1 | 1/2006 | Brockway et al. | |
| 2006/0195149 | A1 | 8/2006 | Hopper et al. | |
| 2006/0206011 | A1 * | 9/2006 | Higgins et al. | 600/300 |
| 2007/0055115 | A1 | 3/2007 | Kwok et al. | |
| 2007/0118183 | A1 | 5/2007 | Gelfand et al. | |
| 2007/0135725 | A1 | 6/2007 | Hatlestad | |
| 2007/0179389 | A1 | 8/2007 | Wariar | |
| 2008/0262360 | A1 | 10/2008 | Dalal et al. | |

FOREIGN PATENT DOCUMENTS

| | | |
|---|---|---|
| EP | 1177764 | 6/2002 |
| WO | WO 9833553 | 6/1998 |
| WO | WO 0240096 | 5/2002 |
| WO | WO 03075744 | 9/2003 |
| WO | WO 2004062485 | 7/2004 |
| WO | WO 2005028029 | 3/2005 |
| WO | WO 2008085309 | 7/2008 |

OTHER PUBLICATIONS

Butler et al., "Beta-Blocker Use and Outcomes Among Hospitalized Heart Failure Patients", Journal of the American College of Cardiology, vol. 47, No. 12, 2006, pp. 2462-2469.

Dark et al., "Breathing Pattern Abnormalities and Arterial Oxygen Desaturation During Sleep in the Congestive Heart Failure Syndrome", Chest, Jun. 1987, 6:833-6. Abstract Only.

Dimopolou I, et al., "Pattern of Breathing during Progressive Exercise in Chronic Heart Failure", IJC 81 (2001), 117-121. Abstract Only.

Duguet et al., "Expiratory Flow Limitation as a Determinant of Orthopnea in Acute Left Heart Failure", Journal of the American College of Cardiology, vol. 35, No. 3, 2000, pp. 690-700.

Hoffman et al., "Cheyne-Stokes Respiration in Patients Recovering from Acute Cardiogenic Pulmonary Edema", Chest 1990, 97:410-12. Abstract Only.

Lee et al., "Predicting Mortality Among Patients Hospitalized for Heart Failure, derivation and validation of a clinical model", JAMA, 2003, 290:2581-87. Abstract Only.

Rame et al., "Outcomes after emergency department discharge with a primary diagnosis of heart failure", American Heart Journal, vol. 142(4), Oct. 2001, pp. 714-719.

Rees et al., "Paroxysmal Nocturnal Dyspnoea and Periodic Respiration", The Lancet, Dec. 22-29, 1979, pp. 1315-1317. Abstract Only.

Solin et al., "Effects of Cardiac Dysfunction on Non-Hypercapnic Central Sleep Apnea", Department of Respiratory Medicine, Alfred Hospital, and Department of Medicine, Monash University Medical School, Melbourne, Victoria, Australia, Apr. 10, 1997, pp. 104-110.

Tkacova et al., "Left Ventricular Volume in Patients with Heart Failure and Cheyne-Strokes Respiration during Sleep", Am. Journal, Respir. Crit. Care Med., vol. 156, pp. 1549-1555, 1997.

Notice of Allowance dated Apr. 7, 2010 from U.S. Appl. No. 11/229,316, 7 pages.

Office Action Response dated Mar. 19, 2010 from U.S. Appl. No. 11/229,316, 8 pages.

Office Action dated Jan. 19, 2010 from U.S. Appl. No. 11/229,316, 12 pages.

Office Action Response dated Sep. 22, 2009 from U.S. Appl. No. 11/229,316, 12 pages.

Office Action dated Jun. 22, 2009 from U.S. Appl. No. 11/229,316, 15 pages.

* cited by examiner

RAPID SHALLOW BREATHING DETECTION FOR USE IN CONGESTIVE HEART FAILURE STATUS DETERMINATION

RELATED PATENT DOCUMENTS

This application is a continuation of U.S. patent application Ser. No. 11/229,316 filed on Sep. 16, 2005, which is incorporated herein by reference in its entirety.

FIELD OF THE DISCLOSURE

The disclosure relates generally to respiration detection and determination of congestive heart failure status based on detected respiratory parameters and/or indices.

BACKGROUND

Rapid shallow breathing (RSB) is a disorder associated with shortness of breath or difficult breathing (the subjective feeling of being out of breath) caused by heart or lung disorders, strenuous activity, high anxiety or stress. One form of RSB, termed dyspnea, derives from interactions among multiple physiological, psychological, social, and environmental factors, and may induce secondary physiological and behavioral responses. Dyspnea is different from tachypnea (rapid breathing) and hyperpnea (deep breathing). Tachypnea and hyperpnea can occur with hyperventilation, or over breathing beyond what is required to maintain arterial blood gases within normal limits. Fear or anxiety may create even more distress in dyspneic patients.

Dyspnea may be classified as chronic, acute, or terminal. Chronic dyspnea has a variable intensity and is associated with persistent shortness of breath. This is most often seen in patients with chronic obstructive pulmonary disease (COPD). Acute dyspnea causes episodes of shortness of breath with high intensity. It may be seen in patients who have suffered a myocardial infarction or pulmonary embolism. Terminal dyspnea occurs in patients with end-stage diseases, and these patients may be in a hospital, at home, or in a hospice. This type of dyspnea is a common complaint in patients with cancer. Dyspnea can be caused by a variety of conditions, including metabolic, allergic, psychiatric, and neuromuscular disorders, and by pain. However, cardiac and pulmonary disorders are the most common causes.

It is estimated that nearly one million hospital admissions for acute decompensated congestive heart failure (CHF) occur in the United States each year, which is almost double the number admitted 15 years ago. The re-hospitalization rates during the 6 months following discharge are as much at 50%. Nearly 2% of all hospital admissions in the United States are for decompensated CHF patients, and heart failure is the most frequent cause of hospitalization in patients older than 65 years. The average duration of hospitalization is about 6 days. Despite aggressive therapies, hospital admissions for CHF continue to increase, reflecting the prevalence of this malady.

SUMMARY

The present invention is directed to systems and methods for detecting changes in respiratory disturbances and changes in congestive heart failure status of a patient. The present invention is further directed to producing trends of respiratory disturbance events and indices developed from such events. The present invention is also directed to systems and methods of adjusting therapy or indicating need for clinical intervention responsive to respiratory disturbance data and trends.

According to various embodiments, methods of the present invention involve providing a medical device comprising sensing circuitry. The medical device may be an implantable or patient-external medical device. One or more respiratory parameters are detected using the device. Patient baseline weight is provided, and an output signal indicative of a patient's congestive heart failure status is generated based on a change in the one or more respiratory parameters and a change in patient weight relative to the patient baseline weight.

The respiratory parameters may include one or more of respiration rate, relative tidal volume, an index indicative of rapid shallow breathing, an index derived by computing a respiration rate and a tidal volume for each patient breath, and an index indicative of dyspnea, for example.

Various responses may occur based on the detected and/or computed respiratory parameters. For example, an index indicative of rapid shallow breathing by the patient may be computed, and the index may be used as a basis to triage or discharge the patient. A perceivable signal may be generated indicating a need for clinician intervention, or initiation, adjustment or termination of therapy delivery to the patient. An output signal may be generated and used for facilitating automatic initiation, adjustment or termination of therapy delivery to the patient (e.g., therapy titration).

According to other embodiments, a change in one or more respiratory parameters may be detected. A computation of a change in patient weight may be initiated based on the magnitude of respiratory parameter change. An output signal may be generated in response to the change in the one or more respiratory parameters exceeding a first threshold and the computed change in the patient weight exceeding a second threshold. The first and second thresholds may be updated in response to the detected change in the one or more respiratory parameters exceeding the first threshold and the computed change in the patient weight exceeding the second threshold. It is understood that comparisons of respiratory parameters to thresholds may involve using a cumulative change in the respiratory signals, such as slope of changes, to avoid errors arising from noisy signal values.

Other embodiments are directed to detecting a change in one or more respiratory parameters relative to a first threshold, and predicting a change in patient weight based on the change in the one or more respiratory parameters. For example, predicting the change in patient weight may involve computing a change in respiration rate and deriving coefficients based on a relationship between change in patient weight relative to change in respiration rate. The coefficients may be derived from a linear regression of change in patient weight relative to change in respiration rate.

A baseline relationship between change in patient weight relative to change in respiration rate for a particular patient may be generated. The baseline relationship may be updated in response to a change in therapy delivered to the patient or change in patient condition.

Further embodiments involve computing a change in respiration rate based on the change in one or more respiratory parameters relative to a first threshold, predicting a change in patient weight based on the change in respiration rate, and generating an output signal in response to the predicted weight change exceeding a second threshold. The method may further involve updating the first and second thresholds in response to the detected change in the one or more respiratory parameters exceeding the first threshold and the predicted weight change exceeding the second threshold.

Various respiratory parameters and weight (actual or predicted) values may used to validate each other. For example, an errant weight value may have resulted from the patient incorrectly following a weight measurement procedure. The change in respiration rate, for example, may be used to validate the weight measurement, such as by determining if the actual weight measurement is reasonable relative to an estimate weight value developed from respiration rate change data. Other forms of signal/measurement/parameter validation are contemplated.

Generating the output signal may be performed at least in part by an implantable medical device. Alternatively, generating the output signal may be performed at least in part by a patient-external system, such as by use of a programmer or networked patient management system.

In accordance with other embodiments of the present invention, a system may be implemented that includes an implantable or patient-external medical device comprising sensing circuitry and detection circuitry coupled to the sensing circuitry. The detection circuitry is configured to detect one or more respiratory parameters. The system further includes a memory configured to store baseline weight of a patient. A processor is coupled to the memory and to the detection circuitry. The processor may be configured to generate an output signal indicative of the patient's congestive heart failure status based on a change in the respiration rate developed from the one or more respiratory parameters and a change in the patient's weight relative to the patient's baseline weight.

In various configurations, the processor and memory may be disposed in a patient-external system. In other configurations, the processor is configured to compute the respiration rate, while in still other configurations the detection circuitry is configured to compute the respiration rate.

The system may include a user interface configured to receive the patient's baseline weight for storage in the memory. The system may also include a weight scale coupled to the user interface and configured to provide the patient's weight. In various embodiments, the processor computes a prediction of the change in the patient's weight based on the change in the respiration rate, and is configured to generate an output signal based on the change in the respiration rate and the predicted change in the patient's weight.

The sensing circuitry may include a transthoracic impedance sensor for sensing respiratory activity of the patient. Alternatively, the sensing circuitry may include an accelerometer for sensing respiratory activity of the patient.

In accordance with further embodiments of the present invention, methods involve providing an implantable or patient-external medical device comprising sensing circuitry, and detecting breaths taken by a patient using the device. An index indicative of rapid shallow breathing by the patient is derived using the detected breaths. A change in congestive heart failure status of the patient is detected based at least in part on a change in the index over time.

Detecting patient breaths may involve validating respiratory activity of the patient as breaths. Deriving the index may involve computing a respiration rate and a tidal volume for each patient breath, and computing the index based on the computed respiration rate and tidal volume. Detecting episodes of rapid shallow breathing may involve detecting a change in the index or a respiratory parameter that exceeds a predetermined threshold.

The method may involve storing logbook information associated with the detected episodes of rapid shallow breathing. Detecting a change in congestive heart failure status may involve trending episodes of rapid shallow breathing using the index or other respiratory parameters over time. Rapid shallow breathing burden of the patient may also be computed.

A therapy may be adjusted and delivered to the patient based on the detected change in congestive heart failure status of the patient. The efficacy of a therapy delivered to the patient may be determined based on the detected change in congestive heart failure status of the patient.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
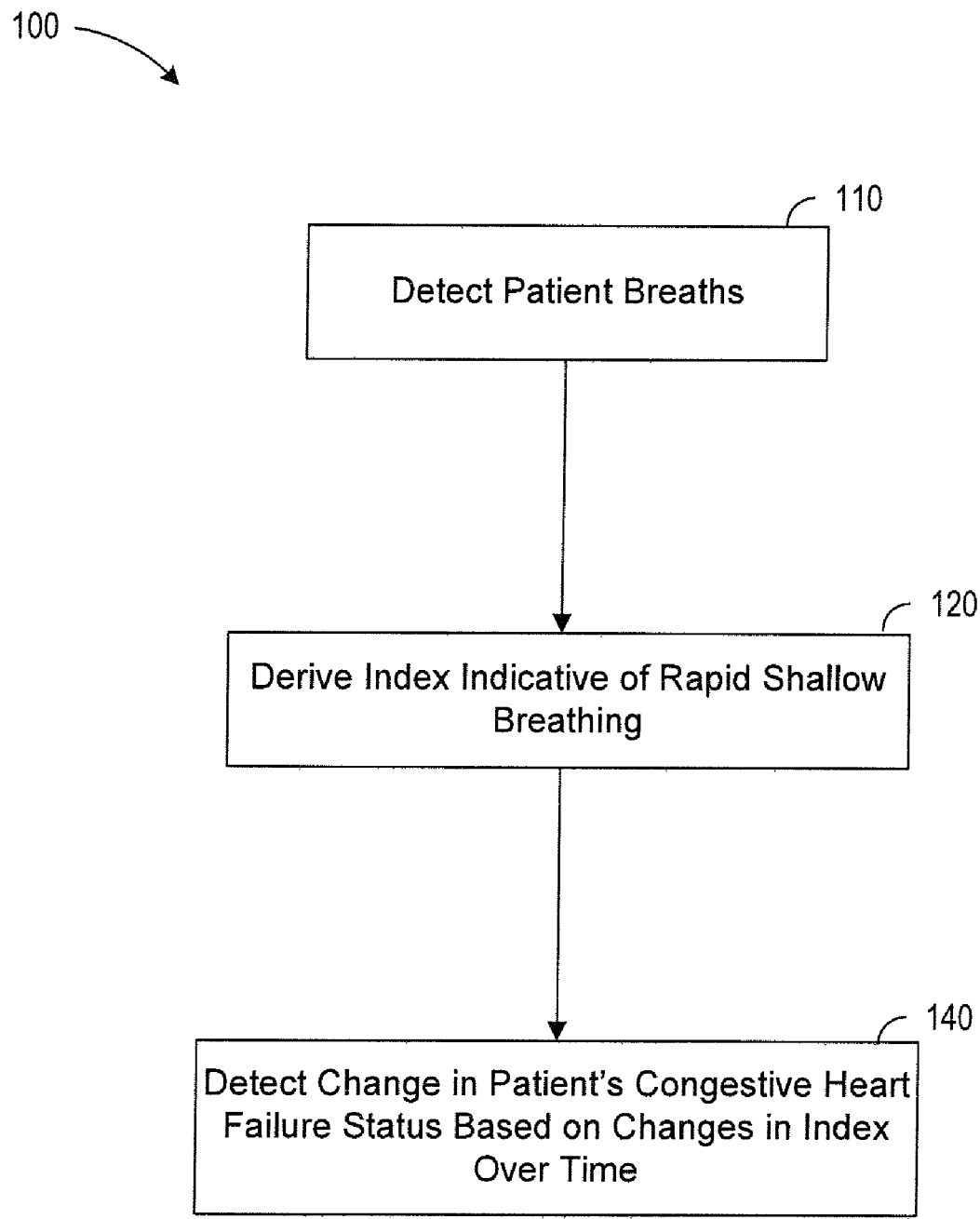
FIG. 1 is a flow diagram of a method for detecting a change in a patient's CHF status based on detected respiratory parameters in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted, partially implanted, or patient-external device need not include all of the features described herein, but may be implemented to include selected features that provide for useful structures and/or functionality. Such a device may be implemented to provide a variety of therapeutic or diagnostic functions.

A wide variety of implantable medical devices, such as cardiac sensing and/or stimulation devices, may be configured to implement a rapid shallow breathing detection methodology of the present invention. A non-limiting, representative list of such devices includes cardiac monitors, pacemakers, cardiovertors, defibrillators, resynchronizers, and other cardiac sensing and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Such devices are referred to herein generally as a patient-implantable medical device (PIMD) for convenience.

The present invention is directed to systems and methods for detecting changes in respiratory disturbances and changes in congestive heart failure status of a patient. Respiratory disturbances, such as rapid shallow breathing, may be monitored using an implantable or patient-external device or sensing arrangement. RSB events may be detected and monitored, and trends in RSB events may be used to detect or indicate changes in a patient's CHF status. Detection of such changes may be used to initiate, adjust or terminate therapy delivery to the patient (via manual or automatic means), or to indicate need for interventional action by the patient or clinician (e.g., an alert/alarm or call to physician).

Therapies delivered to the patient may include drug therapies, such as diuretics, dosages of which may be adjusted. Other therapies may involve cardiac stimulation therapy, such as by use of a cardiac resynchronizer device that increases the patient's heart rate a modest amount, for example 5 to 10 beats per minute, to adapt the heart rate to the patient's need for oxygen. Further therapies may involve respiratory therapies, such as therapies delivered via a continuous positive airway pressure (CPAP) device, which may also provide for pharmacological agent delivery via the CPAP device. It is noted that a CPAP, other type of positive airway pressure device or ventilator, or elastic respiratory band arrangement as is known in the art may be used to detect patient respiration in accordance with the principles of the present invention. Examples of useful respiration detection techniques and disordered breathing therapies are disclosed in commonly-owned U.S. Pat. Nos. 7,252,640 and 7,591,265, which are hereby incorporated herein by reference.

Rapid shallow breathing, such as dyspnea, is typically secondary to pulmonary edema and a common symptom in patients requiring hospitalization for congestive heart failure exacerbation. Embodiments of the invention are directed to monitoring aspects of respiration using patient-implantable or patient-external sensing for monitoring the status of CHF patients. A primary benefit of such monitoring is the identification and possible prediction/prevention of heart failure decompensation episodes. A patient-implantable sensing capability according to the present invention may be viewed as an "early warning system" for heart failure decompensation, utilization of which may lead to reduced hospitalization, improved quality of life, and possibly reduced mortality for CHF patients with implanted devices. Because of the potential for directly measuring signs associated with RSB, such as dyspnea, monitoring of respiratory parameters in accordance with the present invention provides valuable data for clinicians managing heart failure patients.

Embodiments of the present invention provide for a clinically useful index or a set of indices for monitoring and trending respiratory patterns in response to heart failure disease progression and/or decompensation episodes. Continuous monitoring of physiologic parameters of chronic CHF patients as their condition changes provides for identification of indices that may correlate with and/or be predictive of patient heart failure status. It is recognized that heart failure is a complex, multi-faceted syndrome and that the nature of symptoms will vary greatly from patient to patient. The respiratory disturbance detection features according to embodiments of the present invention find particular usefulness when shortness of breath or changes in respiratory patterns is present when heart failure patients decompensate.

In accordance with embodiments of the present invention, trending of respiratory parameters, respiratory disturbance episodes, and/or respiratory indices (e.g., respiration rate, RSB, and/or RSB indices) may be used to detect or confirm RSB, determine CHF status, predict changes in CHF status, adjust a therapy delivered to a patient, and/or predict patient response to a therapy, among other uses. A respiration rate trending algorithm according to embodiments of the present invention may involve trending of a patients' daily respiration rates, it being understood that trending over a time duration other than daily may be employed.

By way of example, a patient's daily minimum, median, and maximum respiration rates may be trended. The median respiration rate refers to the median of every valid breath detected over the whole day. The daily minimum respiration rate refers to the minimum of 30-minute estimates of respiration rate, it being understood that time estimates other than 30-minute estimates may be used, such as 5- or 10-minute estimates for example. The daily minimum respiration rate is meant to capture periods of lowest respiration rate that typically occurs during sleep. The daily maximum respiration rate refers to the maximum of 30-minute estimates of respiration rate. The daily median and daily minimum respiration rates have been found to provide enhanced indication of a patient's CHF status. It is noted that the daily median respiration rate has shown to be less sensitive to outliers as compared to a daily mean respiration rate.

The severity of RSB, such as dyspnea, may be estimated by computing an RSB index (RSBI), which may be defined as the ratio of respiration rate (RR) and relative tidal volume (TV). RSBI is considered an objective measure of the shortness-of-breath symptom that a patient may experience with a worsening of CHF. The worse the RSB, the shallower (i.e., low TV) and the faster (i.e., high RR) the breath, thus the higher the RSBI. It is expected that an increasing trend in RSBI results when the patient decompensates, or a decreasing trend in RSBI results as the decompensated patient responds to treatments.

The respiration rate and relative tidal volume values are preferably determined by use of implantable sensors, examples of which are discussed hereinbelow. It is understood that external sensor may alternatively be used to detect patient respiration from which respiration and relative tidal volume may be determined. In some embodiments, an impedance sensor, such as a transthoracic impedance sensor, may be used to develop a respiration signal. In other embodiments, an accelerometer may be used to develop the respiration signal. Examples of suitable sensors and techniques for developing a respiration signal are disclosed in commonly-owned U.S. Pat. Nos. 6,076,015, 7,252,640 and 7,591,265, which are hereby incorporated herein by reference.

An RSBI according to the present invention may be determined in several ways using a respiration signal developed by an implantable or patient-external sensor. According to one approach, the five-minute median of the breath-by-breath relative TV for all valid breaths is determined. The five-minute median of the breath-by-breath RR for all valid breathes is determined. The five-minute median RSBI is computed as RSBI=(five-minute median of RR)/(five-minute median of TV). The daily median is determined by taking the median of the five-minute median RSBI values over a 24-hour period, starting at the same time each day, such as at 8:00 AM every day.

Relative tidal volume may be determined by finding the maximum and minimum value for each breath, which may be found between the previous and present valid upsloping zero-crossing point of the respiration signal. The difference between the maximum and minimum values is determined. The median of the breath-by-breath relative TV over a five-minute window may be determined. The daily median is determined by taking the median of the five-minute median TV values over a 24-hour period, starting at the same time each day, such as at 8:00 AM every day.

The two respiratory measures, RR and RSBI, are direct measures of the severity of RSB, which is secondary to pulmonary edema in most of CHF patients. Worsening or improvement in pulmonary edema, for example, is associated with the retention or loss of fluid in the lung, which are reflected on weight gain or loss. As such, there exists a strong correlation between patient weight change and respiratory measures change. In particular, the percentage change in RR and RSBI is strongly correlated with percentage change in weight. The relationship between patient weight change and respiratory measures change is advantageously exploited by embodiments of the present invention.

Embodiments of the present invention are directed to monitoring and/or assessing the status and/or progression of CHF based on patient respiration and patient weight. More particularly, changes in patient respiration and weight are detected, and the status and/or progression of CHF is determined. In various embodiments, a patient's baseline weight is determined, and subsequent weight data is acquired based on the patient's actual weight. A weight scale is typically used to acquire the patient's actual weight. Changes in respiration rate and patient weight are evaluated to determine the status and/or progression of a patient's CHF condition.

In other embodiments, changes in patient weight is predicted or estimated based on changes in respiration rate. Predicting changes in patient weight is predicated on the strong correlation between the percentage change in RR (and RSBI) and percentage change in weight. A mathematical or graphical relationship or model of change in weight to change in respiration rate may be developed (e.g., a weight change prediction curve). This relationship or model may be developed using clinical data for a population of patients or developed from data for individual patients.

For example, an individualized relationship or model may be developed for a particular patient using respiratory and weight data acquired during a baseline or training period. The data acquired during this baseline period may be used to develop a plot of percentage change in weight along the x-axis and percentage change in respiratory rate along the y-axis. After termination of the baseline period, changes in patient weight are predicted based on detected changes in respiration rate and coefficients derived from the relationship or model of change in weight to change in respiration rate developed during baseline training. It may be desirable or necessary to update the model, such as when a significant change in therapy occurs or the patient's condition changes significantly.

Figure 12:
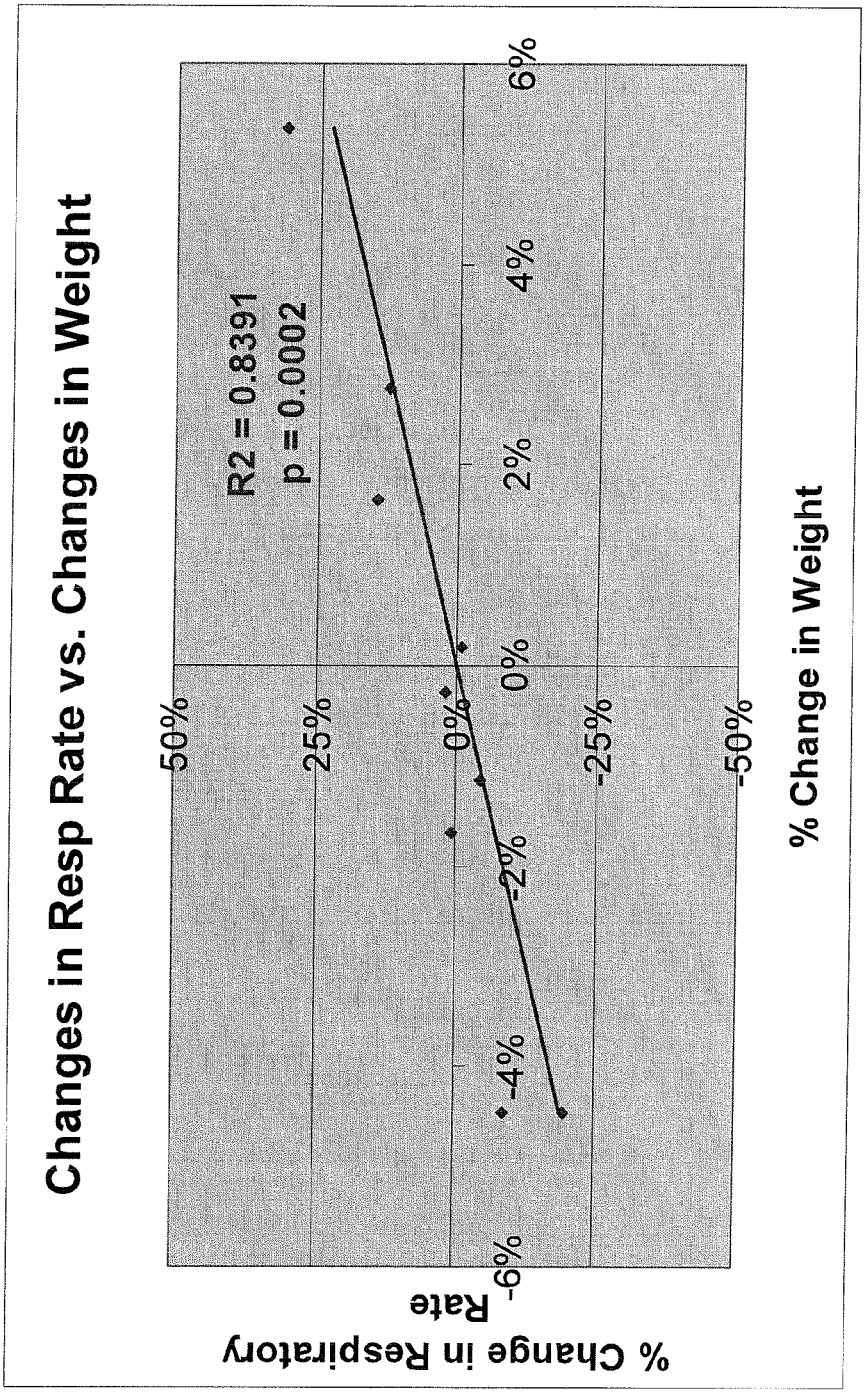
FIG. 12 is a plot showing a correlation between percent change in respiratory rate and percent change in patient weight, from which patient weight change predictions may be computed based on changes in respiratory rate in accordance with embodiments of the present invention.
Figure 13:
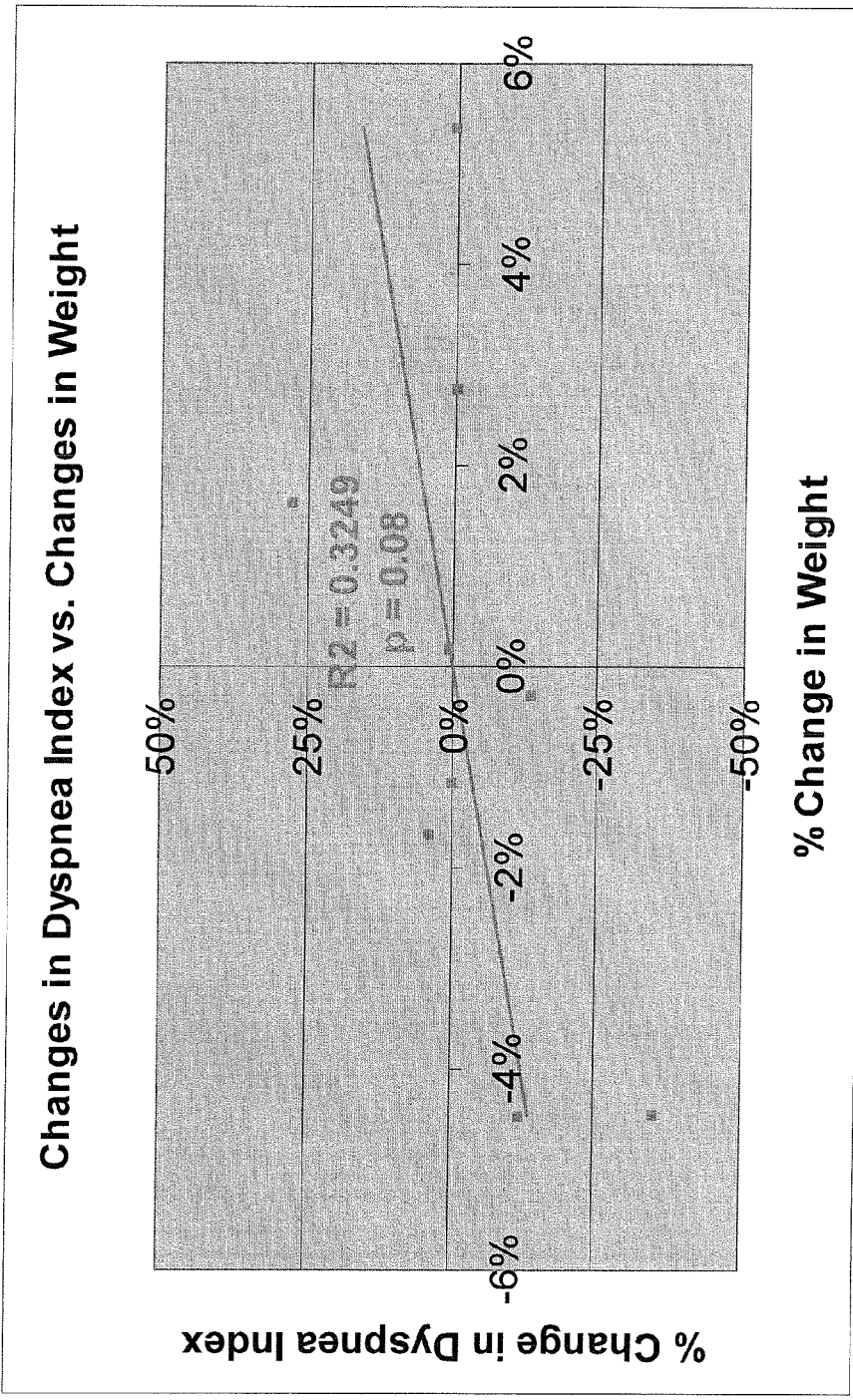
FIG. 13 is a plot showing a correlation between percent change in a dyspnea index and percent change in patient weight, from which patient weight change predictions may be computed based on changes in the dyspnea index in accordance with embodiments of the present invention.

For example, coefficients may be derived from a linear regression performed on the $\Delta$weight to $\Delta$RR data relationship. A change in patient weight may be predicted using the following equation:

$$\Delta \text{Weight} = \Delta RR \cdot (a) + (b) \qquad \text{Equation [1]}$$

where $\Delta$RR refers to the change in respiration rate, and "a" and "b" are coefficients derived from a linear regression performed on the $\Delta$weight to $\Delta$RR data relationship, such as that shown graphically in FIGS. 12 and 13. As is indicated in FIG. 13, a change in patient weight may be predicted based on percent change in RSBI (e.g., dyspnea index) to percent change in patient weight.

Prediction of $\Delta$weight according to the present invention is particularly useful in modular system implementations where various components of the system may be added over time. For example, an implantable medical device, such as a cardiac rhythm management device (e.g., CRT device), may be configured to implantably determine respiration rate from which $\Delta$RR may be computed (internally or externally relative to the patient). Although the system may be configured to accept weight scale data, such a scale may not yet be prescribed by the patient's physician. As such, the patient's actual weight may not be available. Hence, provision of predicted or estimated patient weight is highly desirable in such system configurations where actual patient weight is not available, yet needed or desired. It is noted that various decompensation predication algorithms may use patient weight as a data input, and that predicted patient weight determined in a manner described herein may be used as a substitute for actual patient weight in such algorithms.

Turning now to FIG. 1, there is illustrated a method 100 of detecting a change in a patient's CHF status according to an embodiment of the present invention. According to the method 100 of FIG. 1, patient breaths are detected 110. Using the detected breaths, an index indicative of rapid shallow breathing is derived 120. A change in the patient's CHF status is detected 140 based on changes in the index over time.

Figure 2:
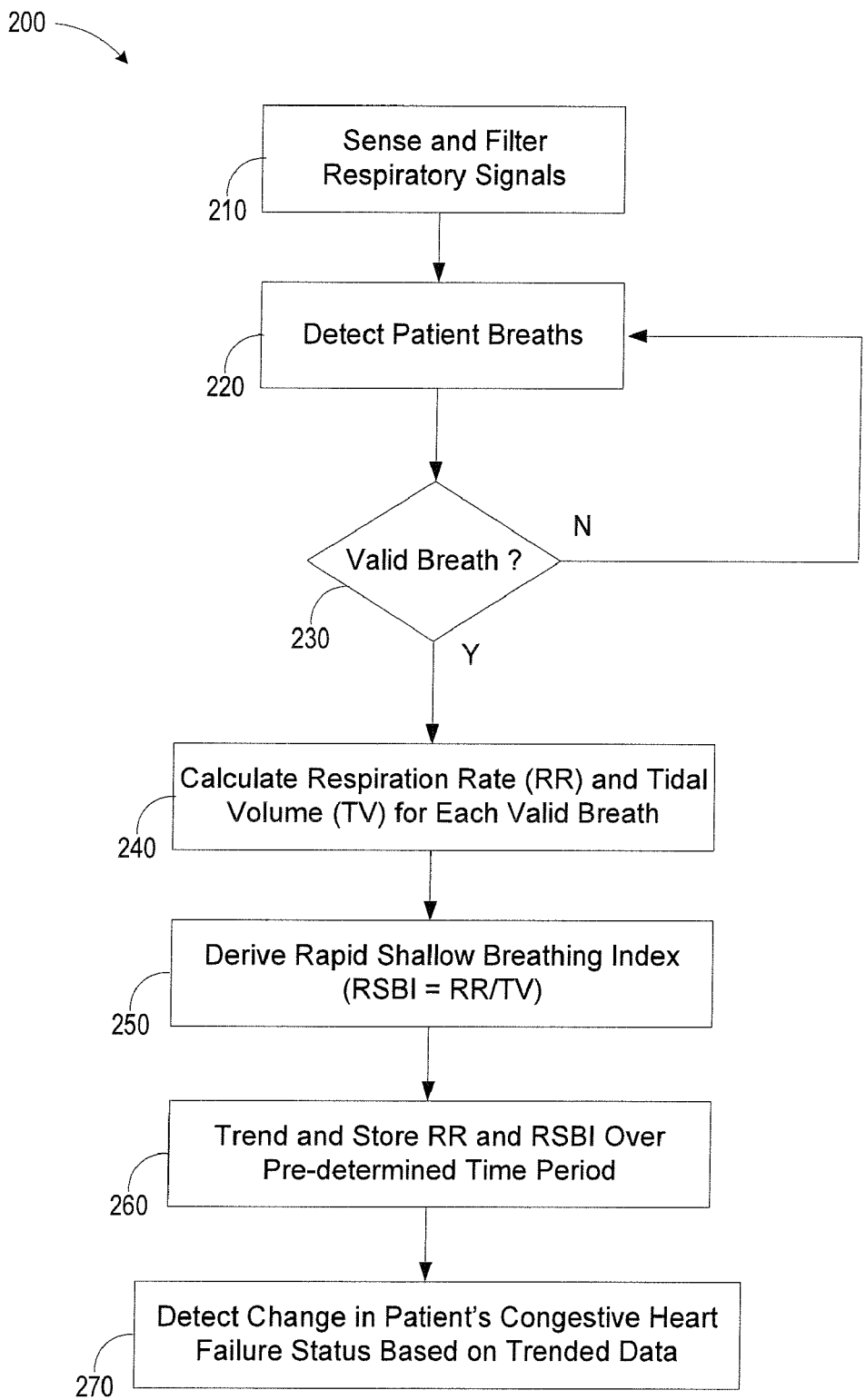
FIG. 2 is a flow diagram of a method for detecting a change in a patient's CHF status based on detected respiratory parameters in accordance with other embodiments of the present invention.

FIG. 2 illustrates a method 200 of detecting a change in a patient's CHF status according to another embodiment of the present invention. According to the method 200 shown in FIG. 2, respiratory signals are sensed and filtered 210. The respiratory signals may be filtered using a variety of techniques. For example, the respiratory signals may be bandpassed filtered to remove the DC component present in the respiratory bands and to minimize the potential influence of noise at frequencies higher than reasonable respiration signals.

Patient breaths are detected 220 using the filtered respiratory signals. Patient breaths may be detected using a variety of techniques. For example, the filtered respiratory signals may be processed with a software zero-crossing breath detection algorithm with hysteresis, such as in accordance with the approach disclosed in commonly-owned U.S. Pat. No. 6,076,015, which is hereby incorporated herein by reference.

The detected patient breaths are further analyzed to determine if such breaths qualify as valid breaths. A valid breath may be determined based on various respiration signal characteristics, such as amplitude and signal morphology, for example. Various known approaches may be employed to discern valid breaths that qualify for inclusion in subsequent processes.

A respiration interval may be determined for the valid breaths. The reciprocal of the respiration interval may be computed to arrive 240 at the respiration rate or RR. The peak amplitude of each valid breath may be detected using a suitable peak detection technique. This peak amplitude may be used to compute 240 relative tidal volume or TV. Using the computed values of RR and TV, a rapid shallow breathing index or RSBI may be computed as RSBI=RR/TV.

The patient's RR and RSBI may be stored and trended 260, such as in a manner described previously above. For example, a five-minute median of the breath-by-breath RR for all valid breathes may be determined, stored, and trended. A five-minute median of the breath-by-breath relative TV for all valid breathes may be determined, stored, and trended.

Other examples include a five-minute median RSBI that may be computed as the five-minute median of RR divided by the five-minute median of TV, which may be determined, stored, and trended. The daily median of RR, TV, RSBI may be determined by taking the median of the five-minute median values over a 24-hour period, starting at the same time (e.g., 8:00 AM) every day, for example. Each of these daily median values may be determined, stored, and trended. Changes in the patient's CHF status may be detected 270 based on this trended data.

Figure 3:
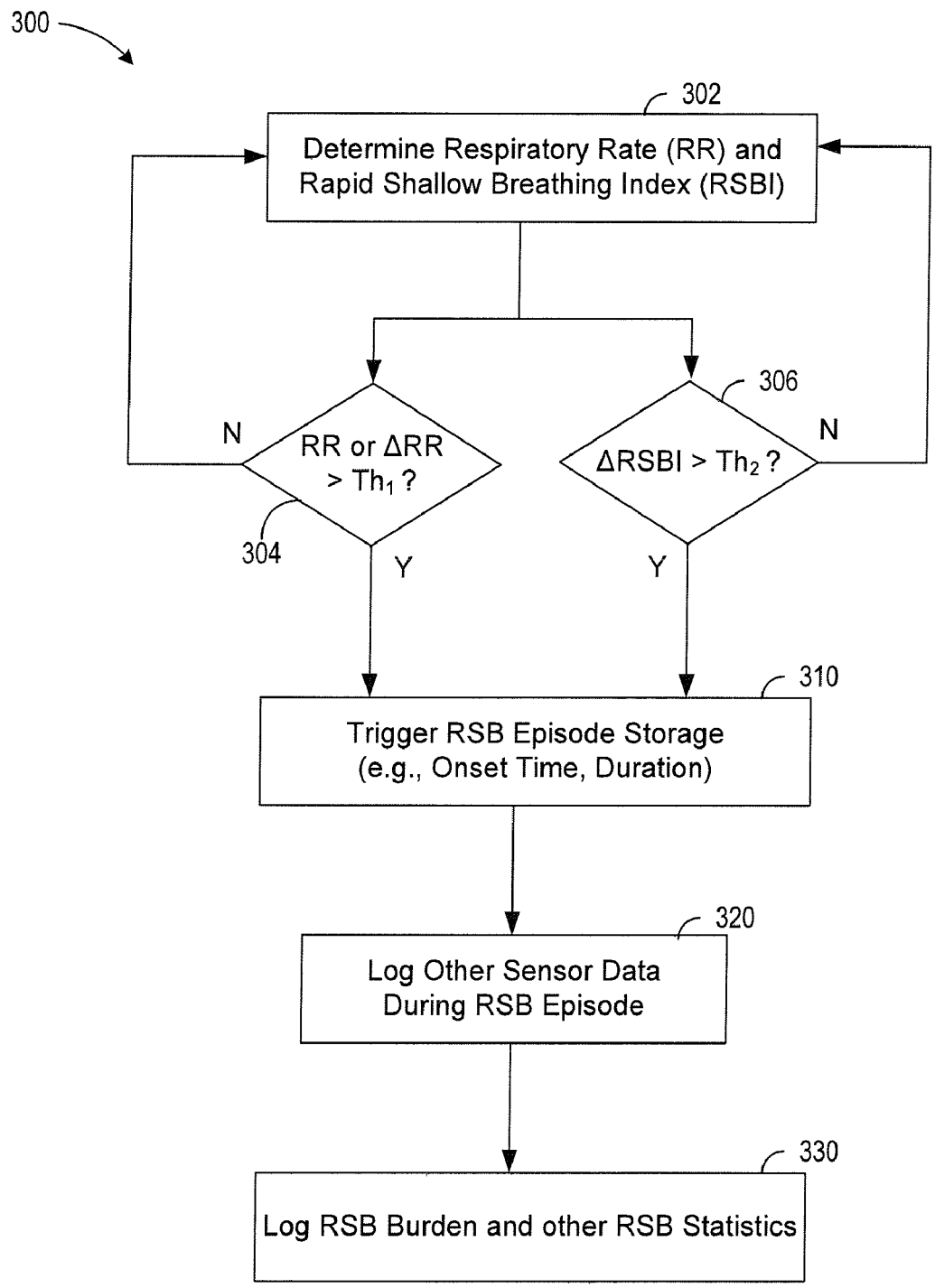
FIG. 3 is a flow diagram of a method for triggering storage of RSB episode data and recording same in a logbook format in accordance with embodiments of the present invention.

FIG. 3 illustrates a method 300 involving trending of RSB episodes. According to the method 300 of FIG. 3, RR and RSBI are determined 302, such as in a manner discussed above. An RSB episode is declare if one or two conditions are present. If RR or changes in RR (ΔRR) exceed a first threshold (Th₁) 304, then an RSB episode is declared. If changes in RSBI (ΔRSBI) exceed a second threshold (Th₂) 306, then an RSB episode is also declared. Satisfaction of either of these tests 304, 306 triggers 310 storage of data acquired during the RSB episode. The onset time and duration of the RSB episode, for example, may be recorded 310. In addition, other sensor data may be recorded 320 during the RSB episode, such as patient activity, posture, heart sounds, implanted transthoracic total impedance sensor measurements, implanted blood pressure sensor measurements or external blood pressure measurements, for example.

RSB burden and other RSB statistics may be developed and logged 330 for the RSB episode. RSB burden, for example, may be computed as the percentage of time a patient experiences RSB per day, average duration of RSB, or other formulation indicating RSB burden on the patient. A daily RSB log may be generated to report a patient's RSB burden.

RSB and other sensor data may be logged, processed, trended, and reported in a manner described in commonly owned U.S. Patent Publication No. 2005/0080348, which is hereby incorporated herein by reference. For example, a logbook may utilize a flat file system, hierarchical database, relational database, or distributed database. Data for a group of RSB events may be analyzed and/or summarized in various formats. Graphical and/or textual summary information may be displayed on the user interface and/or otherwise communicated to the user. For example, histograms, trend graphs, and/or other analytical tools or formats may be generated based on the logbook event entries. A logbook display may display trends and histograms of the patient's RSB rate and index over a predefined time duration, including median, mean, maximum, and minimum respiration rate, RSBI and/or tidal volume values, for example.

Figure 4:
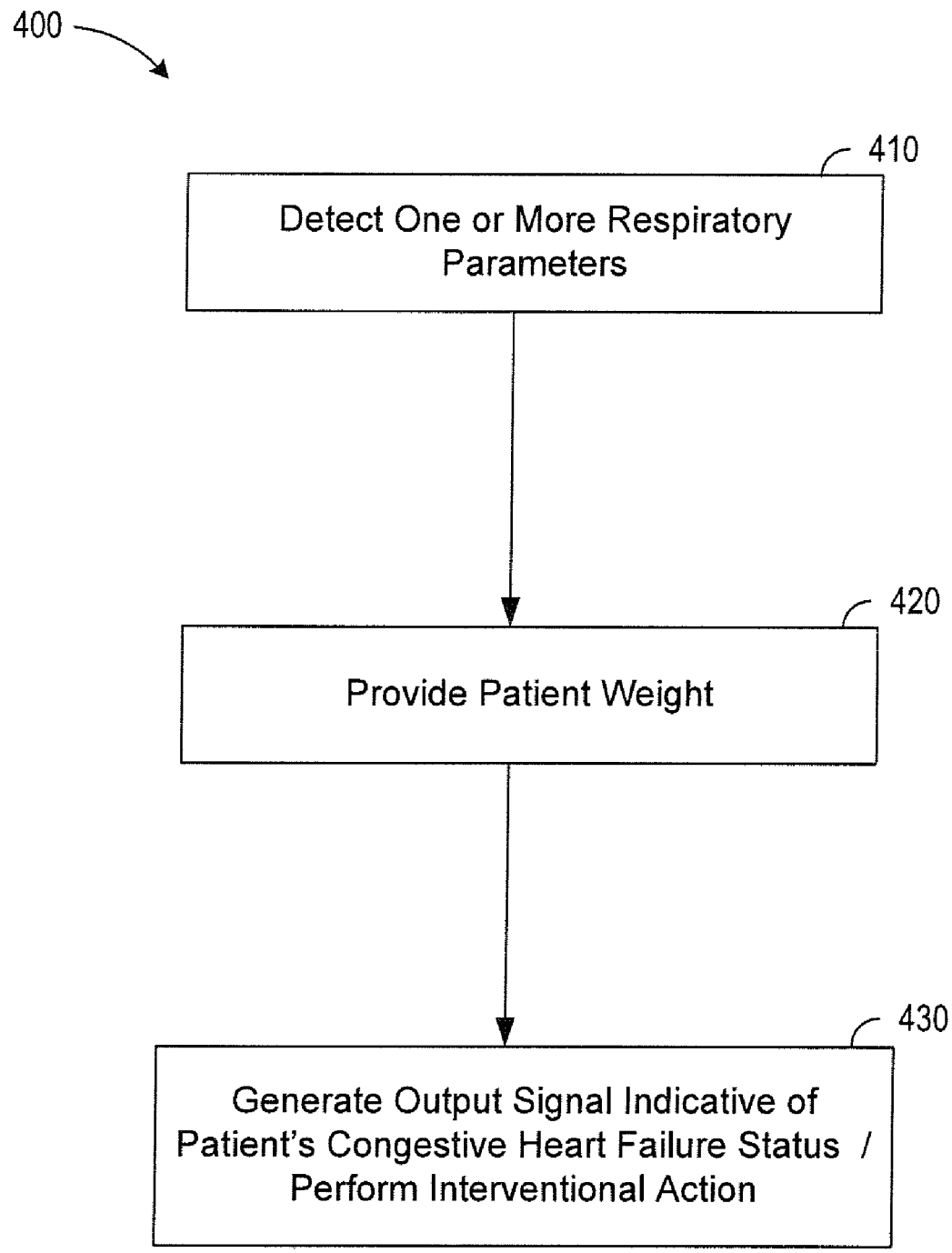
FIG. 4 is a flow diagram of a method for detecting a change in a patient's CHF status based on detected respiratory parameters and patient weight information in accordance with embodiments of the present invention.

FIG. 4 illustrates a method of detecting a patient's CHF status according to another embodiment of the present invention. According to the method 400 shown in FIG. 4, one or more respiratory parameters are detected 410. Patient weight is provided 420. An output signal indicative of the patient's CHF status is generated 430 based on the detected respiratory parameter(s) and the patient's weight. An interventional or diagnostic action may be initiated 430, in combination with or exclusive of, the generation of the output signal. For example, the output signal may initiate computation of an index, such as a rapid shallow breathing index (e.g., dyspnea index), that can be used to triage or discharge the patient.

Therapies that may be administered to treat RSB in response an output signal indicative of a patient's CHF status may include non-pharmacological and pharmacological interventions. For example, treating CHF patients with digoxin and diuretics may help resolve the patient's RSB. Stimulation of mechanoreceptors in the respiratory musculature or over the face has reduced RSB in some patients. Vibration of the intercostal muscles, in phase with inspiration so that contracting respiratory muscles are vibrated, has relieved RSB in some COPD patients. Movement of cool air across the face by a fan or an open window can stimulate mechanoreceptors in the face, minimizing mild RSB. Oxygen, administered by mask or nasal cannula or transtracheally, improves RSB. In patients with COPD, many authorities recommend oxygen therapy for raising PaO2 levels to at least 55 mmHg to 60-mmHg or oxygen saturation to 88% to 90%.

Evidence suggests that opioids, despite their possible respiratory depressant effect, are useful in managing RSB. While the action of opioids to relieve RSB is not fully understood, the drugs may act by blunting the emotional reaction to RSB by interaction with opioid receptors in the limbic system. Because opioids cause euphoria, they reduce fear, anxiety, and the associated restlessness and muscle tension that decrease oxygen consumption. Opioids may also relieve RSB by action on the chemoreceptors, thus reducing respiratory drive.

When RSB becomes intolerable and increased doses of systemic opioids are contraindicated because of unacceptable adverse effects, nebulized morphine may be administered. Nebulized morphine may relieve RSB by direct local action on peripheral opioid receptors in the airways so that it does not reach the systemic concentration to the extent that oral, subcutaneous, or intravenous morphine does. Therefore, some patients experience relief of RSB with fewer adverse effects.

Anxiolytics frequently used to relieve RSB include benzodiazepines and phenothiazines. These act by depressing the hypoxic, hypercapnic response to RSB and the emotional response to RSB. Depending on the cause of RSB, patients may benefit from bronchodilators. Since methylxanthines cause smooth muscle dilation of the airways and improve the contraction of the diaphragm, they may be useful in patients with COPD. Similarly, inhaled beta-2 adrenergic agonists and anticholinergics cause smooth muscle dilation of the airways, thus improving lung mechanics and possibly relieving RSB.

Figure 5:
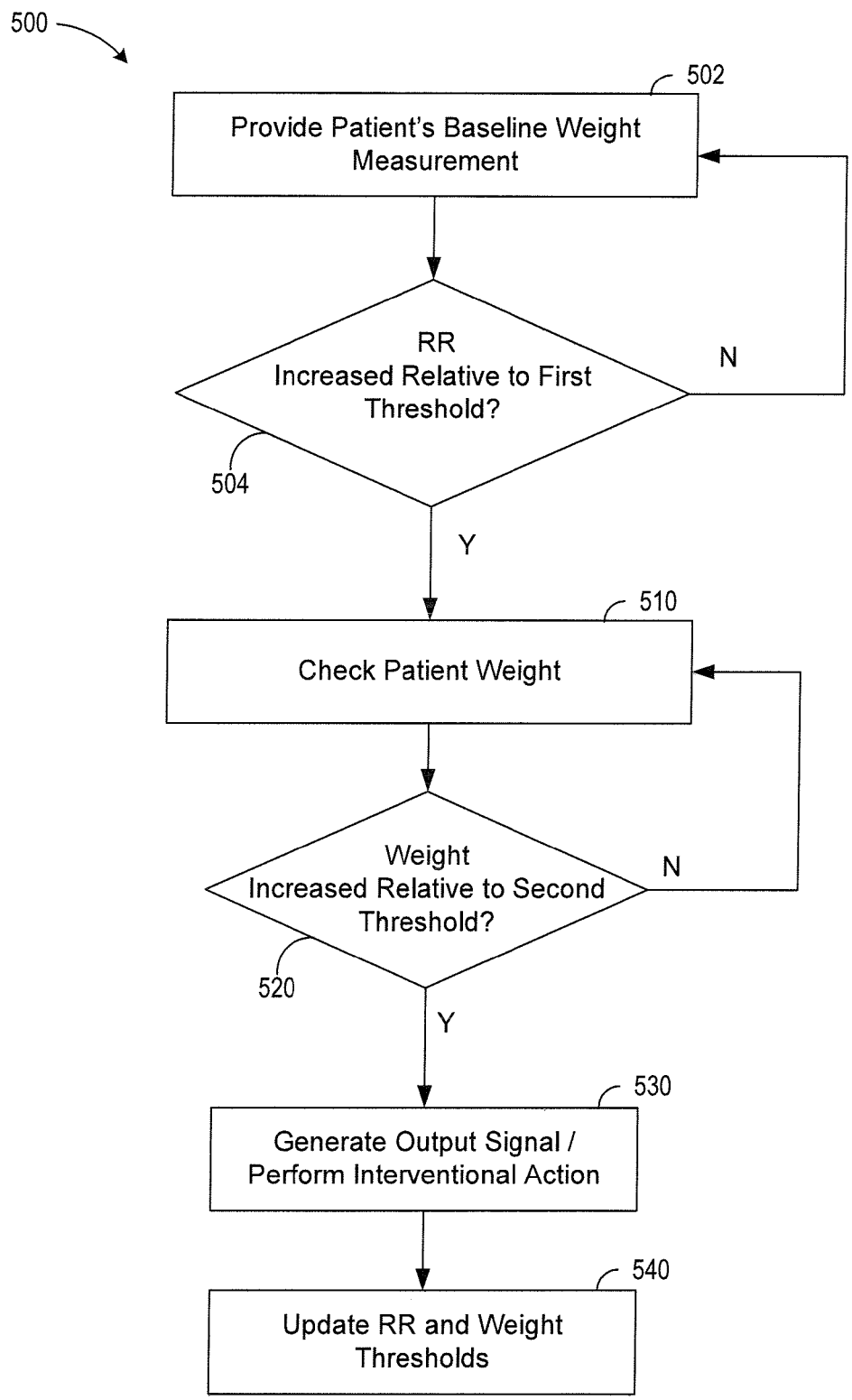
FIG. 5 is a flow diagram of a method for detecting a change in a patient's CHF status based on detected respiratory parameters and patient weight information in accordance with embodiments of the present invention.

FIG. 5 illustrates a method of detecting a patient's CHF status using a patient's actual weight (rather than predicted weight) according to a further embodiment of the present invention. According to the method 500 shown in FIG. 5, a patient's baseline weight measurement is provided 502. The patient's respiratory rate is compared 504 to a first threshold. If the patient's RR exceeds the first threshold, a check 510 is made to determine the patient's weight. If the patient's weight has increased relative to a second threshold 520, an output signal indicative of the patient's CHF status is generated 530 based on the change of the detected respiratory parameter(s) and the patient's weight change. An interventional or diagnostic action may be initiated 530, in combination with or exclusive of, the generation of the output signal.

The first and second thresholds associate with the patient's RR and weight may be updated 540. The patient's RR threshold, for example, may be updated using a previously discussed technique, such as use of a prediction curve of the type described with regard to FIG. 12. The patient's weight threshold may be updated based on clinical data or practice (e.g., 2 lb/day or 5 lb/week change). According to one approach, a patient's weight change may be calculated using Equation [1] above as $\Delta weight=0.1794 \cdot \Delta RR - 0.0031$, where $\Delta RR$ varies between 5-30%. Thresholds for both $\Delta weight$ and $\Delta RR$ may be established by the clinician in accordance with this approach or other suitable methodology.

Figure 6:
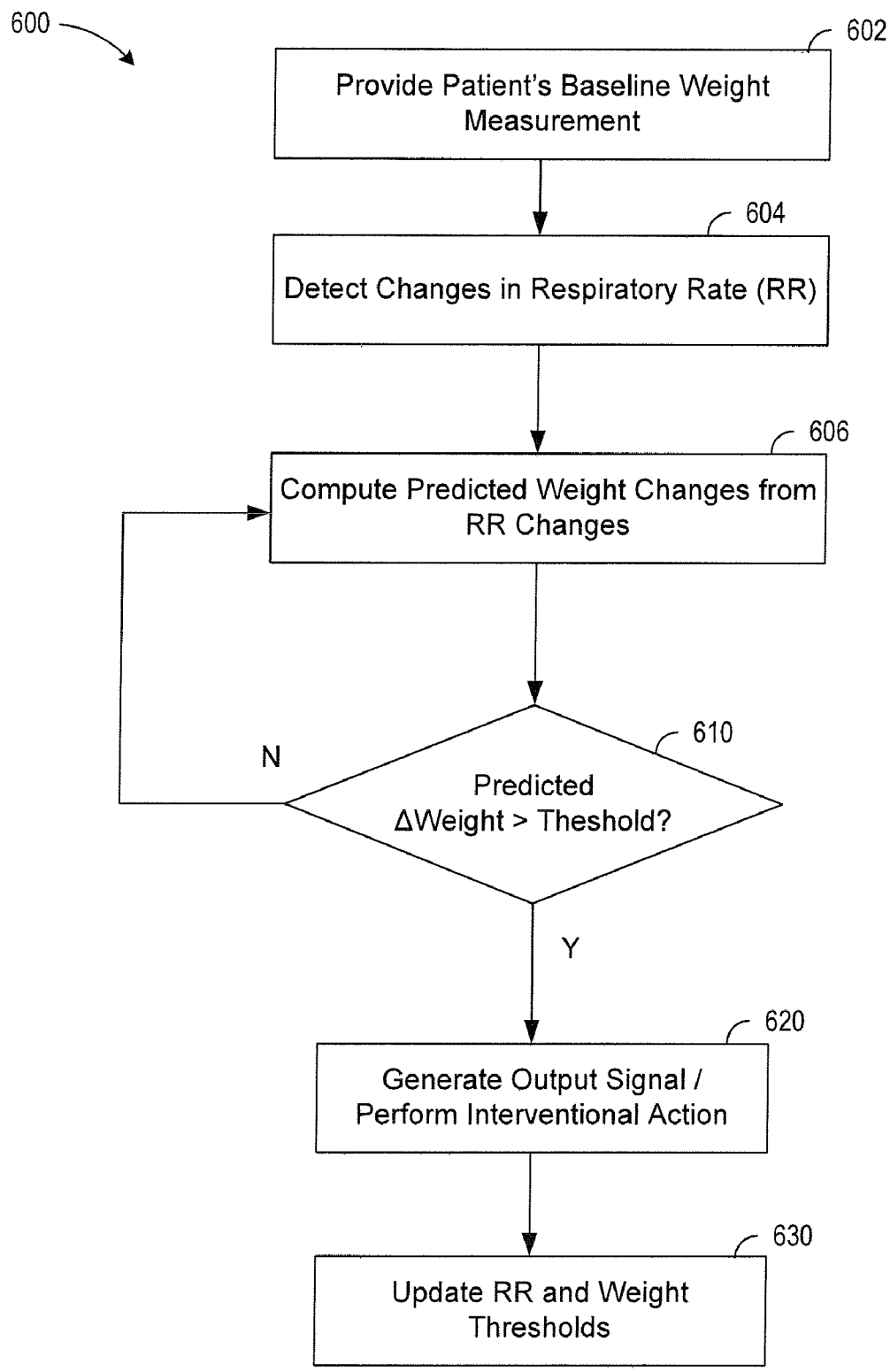
FIG. 6 is a flow diagram of a method for detecting a change in a patient's CHF status based on detected respiratory parameters and predicted patient weight change in accordance with embodiments of the present invention.

FIG. 6 illustrates a method of detecting a patient's CHF status using a patient's predicted weight (rather than actual weight) according to another embodiment of the present invention. According to the method 600 shown in FIG. 6, a patient's baseline weight measurement is provided 602. The patient's respiratory rate is computed and changes in the RR are detected 604. A predicted weight change of the patient is computed 606 based on the changes in RR.

If the predicted change in patient weight exceeds a threshold 610, an output signal indicative of the patient's CHF status is generated 620 based on the patient's RR and predicted change in weight. An interventional or diagnostic action may be initiated 620, in combination with or exclusive of, the generation of the output signal. The thresholds associate with the patient's RR and weight may be updated 630.

Various embodiments described herein may be used in connection with devices that provide for CHF monitoring, diagnosis, and/or therapy. A patient implantable medical device or PIMD of the present invention may incorporate CHF features involving dual-chamber or bi-ventricular pacing/therapy, cardiac resynchronization therapy, cardiac function optimization, or other CHF related methodologies. For example, a PIMD of the present invention may incorporate features of one or more of the following references: commonly owned U.S. Pat. Nos. 7,260,432 and 6,411,848; 6,285,907; 4,928,688; 6,459,929; 5,334,222; 6,026,320; 6,371,922; 6,597,951; 6,424,865; and 6,542,775, each of which is hereby incorporated herein by reference. Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of a type that may benefit from rapid shallow breathing measuring methods and implementations are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of a type that may benefit from rapid shallow breathing measuring methods and implementations are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of a type that may benefit from rapid shallow breathing measuring methods and implementations are disclosed in commonly owned U.S. Pat. Nos. 5,313,953; 5,388,578; and 5,411,031, which are hereby incorporated herein by reference.

Typically, changes in a patient's cardiopulmonary response after a pacemaker or similar device has been implanted are not addressed until the patient is symptomatic, and has gone through a formal clinical evaluation with the use of external gas exchange equipment. A PIMD having rapid shallow breathing measurement capabilities in accordance with the present invention reduces the response time needed to correct the patient's rapid shallow breathing (e.g., dyspnea) problem and/or to introduce additional therapy. A PIMD having rapid shallow breathing measurement capabilities in accordance with the present invention also provides for robust trending of the patient's rapid shallow breathing and CHF status/progression over time.

Figure 7:
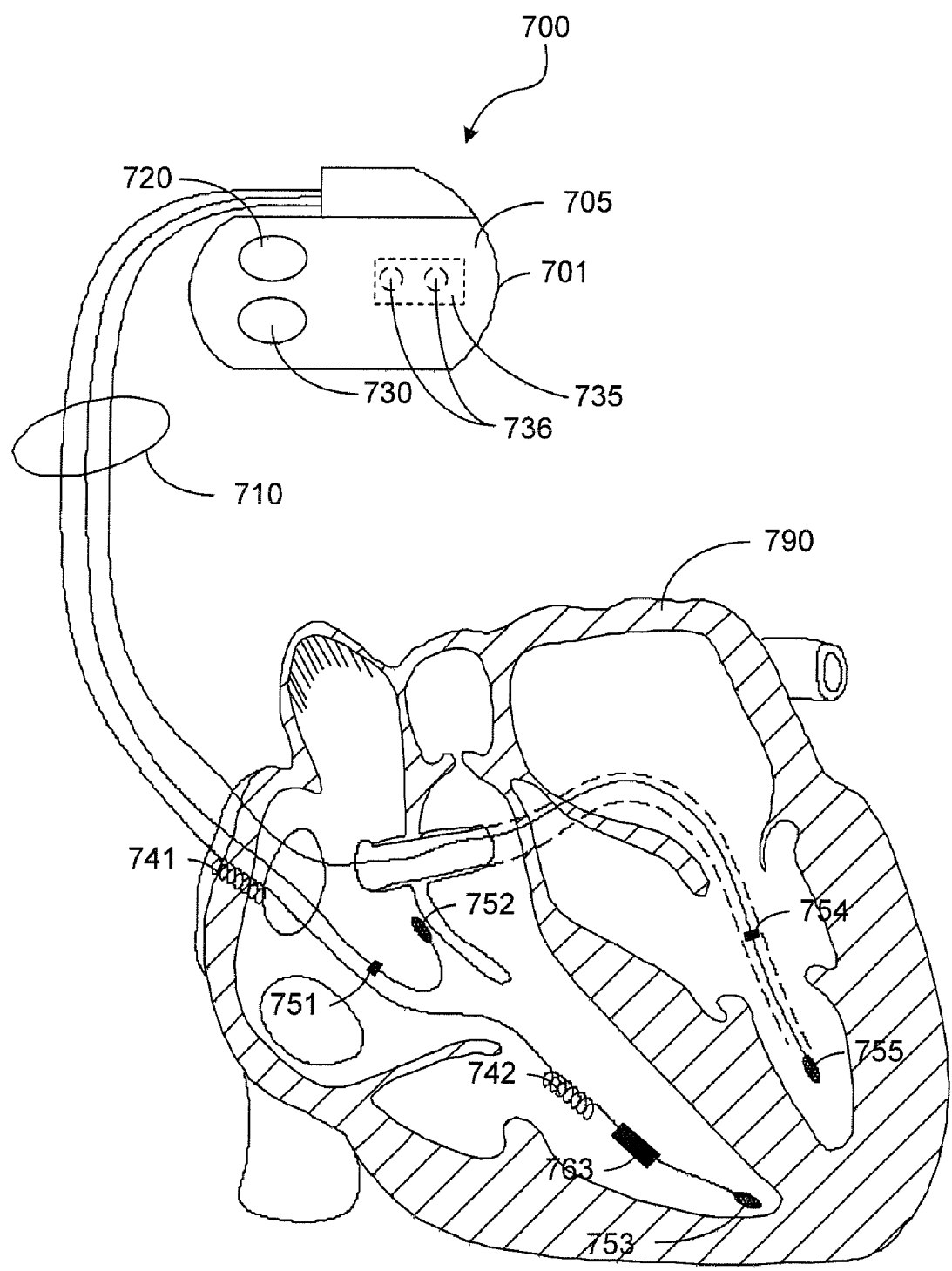
FIG. 7 is an illustration of an implantable cardiac device including a lead assembly shown implanted in a sectional view of a heart, the implantable cardiac device implemented to detect respiratory activity of the patient in accordance with embodiments of the invention.

Referring now to FIG. 7, there is illustrated an embodiment of a PIMD configured to detect changes in a patient's CHF status in accordance with the present invention. In this illustrative example, the PIMD includes a cardiac rhythm management device (CRM) 700 including an implantable pulse generator 705 electrically and physically coupled to an intracardiac lead system 710.

Portions of the intracardiac lead system 710 are inserted into the patient's heart 790. The intracardiac lead system 710 includes one or more electrodes configured to sense electrical cardiac activity of the heart, deliver electrical stimulation to the heart, sense the patient's transthoracic impedance, sense acceleration and/or body acoustics, and/or sense other physiological parameters, e.g., cardiac chamber pressure or temperature. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station, external programmer or patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to develop a respiration waveform from which RR, RSBI, TV, and other respiratory parameters may be developed and used in accordance with embodiments of the present invention.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 7, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 7 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

For purposes of illustration, and not of limitation, various embodiments of devices that may use rapid shallow breathing measurement in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending US Publication No. 2004/0230230 and U.S. Pat. No. 7,499,750, which are hereby incorporated herein by reference.

Figure 8:
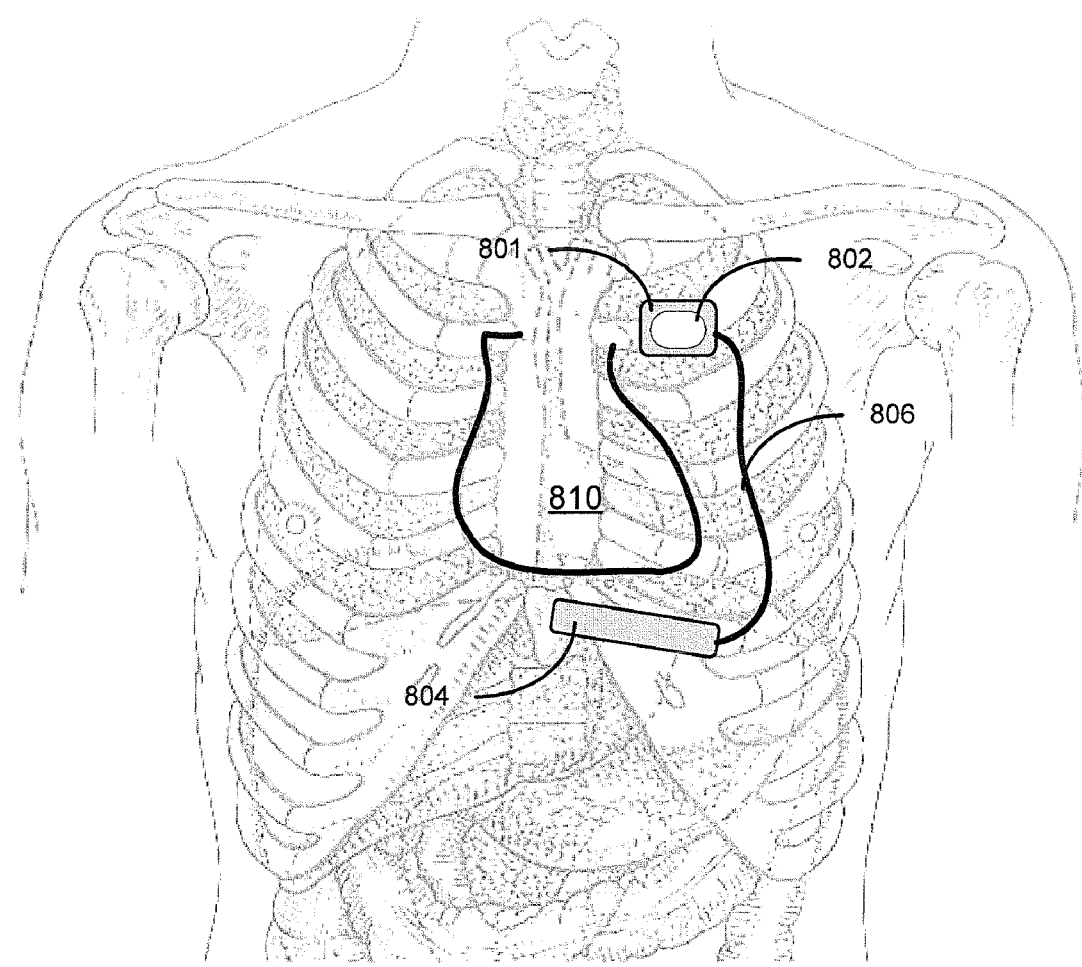
FIG. 8 is an illustration of an implantable cardiac device including a subcutaneous, non-intrathoracic lead assembly shown implanted outside the ribcage, the implantable cardiac device implemented to detect respiratory activity of the patient in accordance with embodiments of the invention.

In one configuration, as is illustrated in FIG. 8, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation. For example, portions of the housing 801 may be covered with a non-conductive, or otherwise electrically resistive, material to direct current flow. Suitable non-conductive material coatings include those formed from silicone rubber, polyurethane, or parylene, for example.

Figure 9:
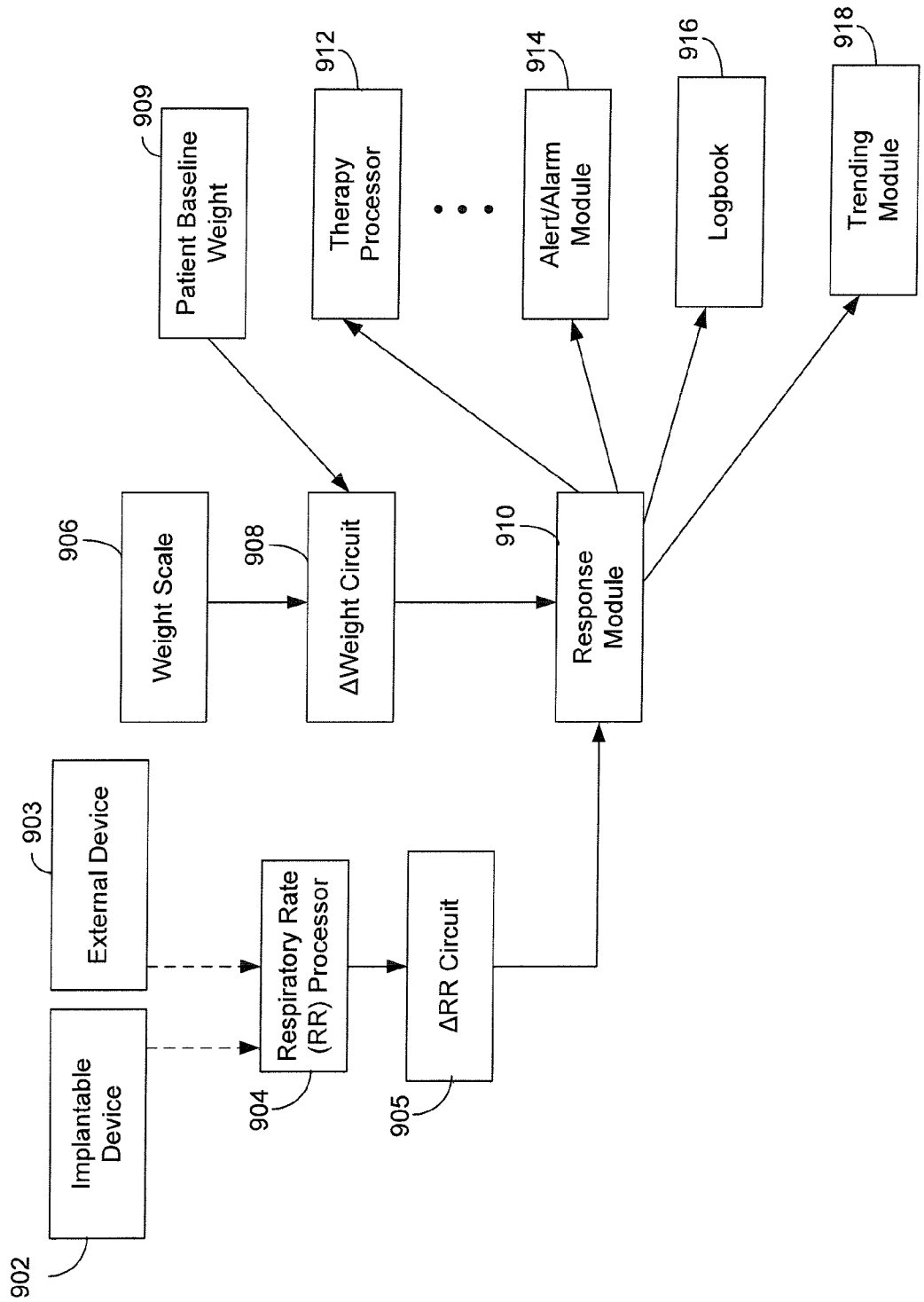
FIG. 9 is a block diagram showing components of a system for acquiring respiratory parameters and patient weight, and detecting a patient's CHF status or change in CHF status using the acquired respiratory and weight information in accordance with embodiments of the present invention.

FIG. 9 is a block diagram showing components of a system for acquiring respiratory parameters and patient weight, and detecting a patient's CHF status or change in CHF status using the acquired respiratory and weight information. The embodiment shown in FIG. 9 includes an implantable device 902, which may be configured as a PIMD as described herein or other implantable or patient-external device implemented to detect patient respiration. Patient-external device 903 is also shown in FIG. 9. Either of the implantable or external devices 902, 903 may be used to detect patient respiration. It is understood that both devices 902, 903 need not be used, but that both as shown as possible system configuration options.

The implantable device 902 (or external device 903) incorporates or is coupled to a respiratory rate processor 904. The RR processor 904 processes sensed respiratory activity and computes a respiration rate of the patient. The RR data is communicated from the RR processor 904 to a ΔRR circuit 905. The ΔRR circuit 905 compares the RR data to a preestablished threshold, and generates a threshold signal when the patient's RR exceeds the threshold. The threshold signal is communicated from the ΔRR circuit 905 to a response module 910. It is noted that the RR processor 904 and ΔRR circuit 905 are typically disposed in the implantable device 902. It is further noted that one or both of the RR processor 904 and ΔRR circuit 905 may alternatively be disposed in a device external to the patient (e.g., external device 903, programmer, or patient management system).

In the embodiment shown in FIG. 9, a weight scale 906 is available and used to acquire patient weight. The measured patient weight is communicated (electronically or via manual input) to a Δweight circuit 908. The Δweight circuit 908 compares the weight data to a preestablished threshold, and generates a threshold signal when the patient's weight exceeds the threshold relative to the patient's baseline weight 909. The threshold signal is communicated from the Δweight circuit 908 to the response module 910.

The response module 910 receives threshold signals from the ΔRR circuit 905 and Δweight circuit 908. The response module 910 may also receive raw and/or processed respiratory and weight data respectively from the ΔRR and Δweight circuits 905, 908. The response module 910 may be implemented to provide various output signals and functionality. The response module 910, for example, may generate a signal indicative of the patient's CHF status, progression, and/or predicted status/progression based on the outputs from the ΔRR and Δweight circuits 905, 908. The response module 910 may also generate a signal that is used by a therapy processor 912 to initiate, adjust, or terminate a therapy delivered to the patient, such as a diuretics therapy. The response module 910 may also generate a signal that is received by an alert/alarm module 914. Alert/alarm module 914 produces a perceivable alert that indicates the patient requires clinician attention or intervention in response to the generated signal.

The response module 910 may further produce a signal that initiates generation of respiratory statistics using a logbook 916. An index, such as RSBI, may be calculated in response to the response module signal, and trending of the index and other respiratory parameters, such as RR and TV, may be performed by a trending module 918. This data may be used to assess the patient's CHF status, predict the patient's CHF status, triage or discharge a patient, alert clinicians, and/or to adjust therapy (via a therapy processor 912) delivered to the patient, among other functions.

Figure 10:
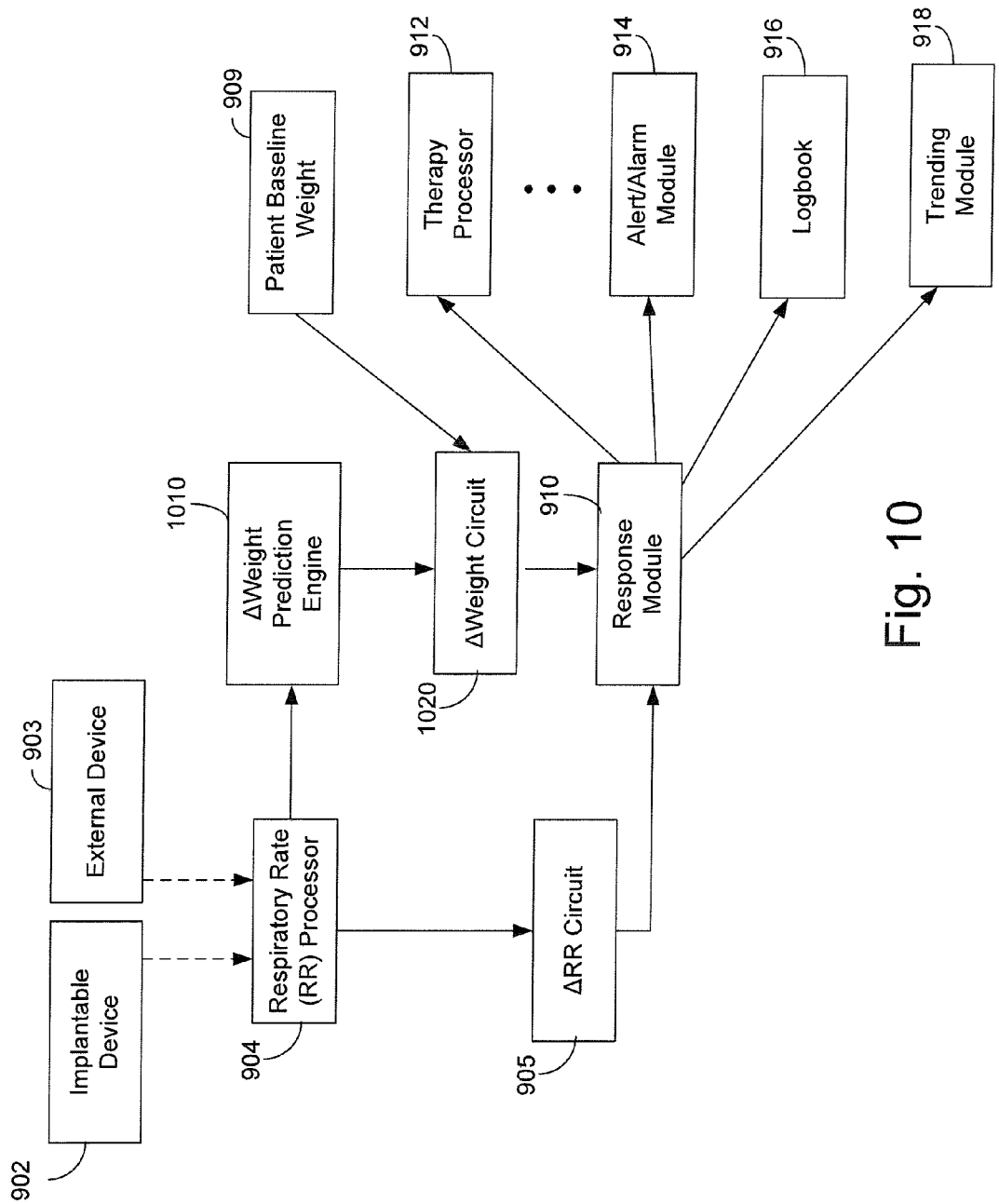
FIG. 10 is a block diagram a system for acquiring respiratory parameters and detecting a patient's CHF status or change in CHF status using the acquired respiratory information and predicted patient weight change data in accordance with embodiments of the present invention.

FIG. 10 is a block diagram a system for acquiring respiratory parameters and detecting a patient's CHF status or change in CHF status using the acquired respiratory information and predicted patient weight change data. The embodiment shown in FIG. 10 includes an implantable device 902 and patient-external device 903 of a type described above with regard to FIG. 9.

The implantable device 902/external device 903 incorporates or is coupled to a respiratory rate processor 904. The RR processor 904 processes sensed respiratory activity and computes a respiration rate of the patient. The RR data is communicated from the RR processor 904 to a ΔRR circuit 905. The ΔRR circuit 905 compares the RR data to a preestablished threshold, and generates a threshold signal when the patient's RR exceeds the threshold. The threshold signal is communicated from the ΔRR circuit 905 to a response module 910.

In the embodiment shown in FIG. 10, a weight scale is not available. A prediction of the patient's weight change is computed by a Δweight prediction engine 1010 based on the patient's baseline weight 909 and changes in respiratory rate as described hereinabove. A Δweight circuit 1020 compares the predicted weight change data to a preestablished threshold, and generates a threshold signal when the patient's predicted weight exceeds the threshold. The threshold signal is communicated from the Δweight circuit 1020 to the response module 910.

The response module 910 receives threshold signals from the ΔRR circuit 905 and Δweight circuit 1020. The response module 910 may also receive raw and/or processed respiratory and predicted weight data respectively from the ΔRR and Δweight circuits 905, 1020. The response module 910 may be implemented to provide various output signals and functionality, such as those described previously with regard to the embodiment illustrated in FIG. 9.

Figure 11:
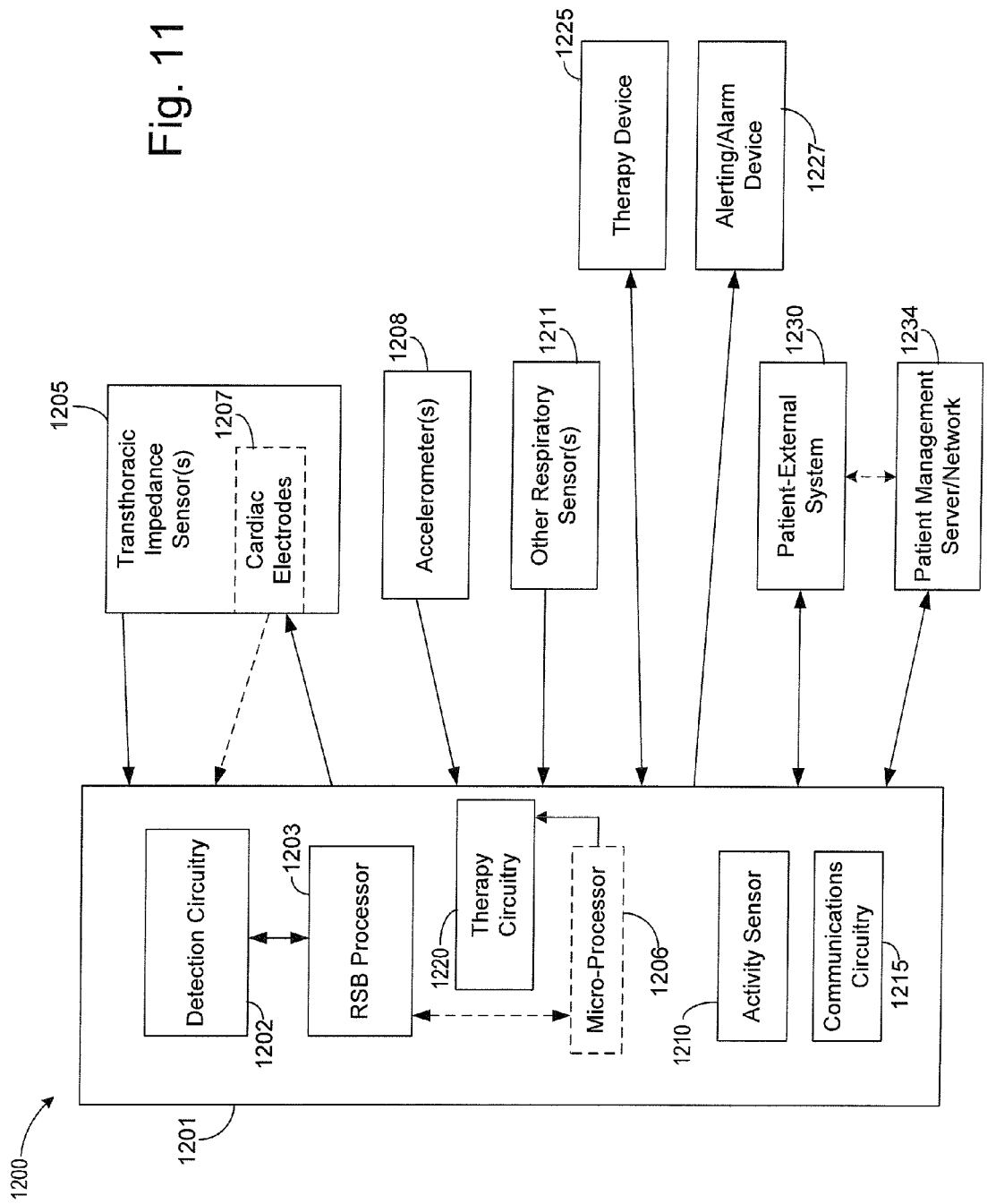
FIG. 11 is a block diagram of a patient-implantable medical device configured to include cardiac sensing and/or stimulation features in addition to respiratory sensing capabilities in accordance with embodiments of the present invention.

FIG. 11 is a block diagram of a PIMD 1200 that is configured to include cardiac sensing and/or stimulation features in addition to respiratory sensing capabilities in accordance with an embodiment of the present invention. It is noted that all or selected components of PIMD 1200 shown in FIG. 11 may alternatively be incorporated in a patient-external device or system. PIMD 1200 includes an RSB processor 1203 which may be incorporated into and/or operate in cooperation with a microprocessor 1206. Detection circuitry 1202, which may be coupled to the RSB processor 1203 and/or the microprocessor 1206, may be configured to incorporate, or communicate with, specialized circuitry for processing sensed cardiac signals in manners particularly useful in a cardiac sensing and/or stimulation device. As is shown by way of example in FIG. 11, the detection circuitry 1202 may receive information from multiple physiologic and non-physiologic sensors.

The detection circuitry 1202 receives information from one or more sensor(s) 1205 that monitor transthoracic impedance. As is known in the art, transthoracic impedance sensor(s) 1205 may be the same as or different from one or more cardiac electrodes 1207 used for cardiac sensing and/or stimulation. The RSB processor 1203 is coupled to the sensor(s) 1205 and configured to compute RR, TV, RSBI or other indices indicative of pulmonary function using the sensed transthoracic impedance. An activity sensor 1210 is coupled to the RSB processor 1203 and configured to sense patient activity. The activity sensor 1210 may include an accelerometer in, on, or coupled to the PIMD 602. The activity sensor 1210 or one or more other accelerometers 1208 may be used to sense respiratory activity from which valid breaths may be detected and RR, TV, and RSBI computed.

Therapy circuitry 1220 is coupled to the microprocessor 1206 and configured to provide a therapy at least partly based on the respiratory parameters and/or indices determined by the RSB processor 1203. Therapy circuitry 1220 is also coupled to one or more of the cardiac electrodes 1207 and configured to deliver a cardiac therapy as appropriate.

Communications circuitry 1215 is coupled to the microprocessor 1206. The communications circuitry 1215 allows the PIMD 1200 to communicate with one or more receiving devices or systems 1230 situated external to the PIMD 1200. By way of example, the PIMD may communicate with a patient-worn, portable or bedside communication system via the communications circuitry 1215. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD 1200 via the communications circuitry 1215. It is noted that physiologic or non-physiologic sensors equipped with wireless transmitters or transceivers may communicate with a receiving system external of the patient.

The communications circuitry 1215 preferably allows the PIMD 1200 to communicate with an external programmer 1230. In one configuration, the communications circuitry 1215 and the programmer unit 1230 use a wire loop antenna and a radio frequency telemetric link, as is known in the art, to receive and transmit signals and data between the programmer unit 1230 and communications circuitry 1215. In this manner, programming commands and data are transferred between the PIMD 1200 and the programmer unit 1230 during and after implant. Using a programmer 1230, a physician is able to set or modify various parameters used by the PIMD 1200. For example, a physician may set or modify parameters affecting sensing, detection, pacing, and defibrillation functions of the PIMD 1200, including pacing and cardioversion/defibrillation therapy modes. The programmer unit 1230 may also be used to input patient baseline weight, set and modify thresholds, and initiate and view RSB trend data, among other functions.

The PIMD 1200 may detect a variety of physiological signals using various respiratory and other sensors 1211 that may be used in connection with various diagnostic, therapeutic or monitoring implementations. For example, the PIMD 1200 may include sensors or circuitry for detecting respiratory system signals, cardiac system signals, and signals related to patient activity. In various embodiments, the PIMD 1200 senses intrathoracic impedance or acceleration, from which various respiratory parameters may be derived, including, for example, respiratory rate, relative tidal volume and minute ventilation. Sensors and associated circuitry may be incorporated in connection with a PIMD 1200 for detecting one or more body movement or body posture or position related signals. For example, accelerometers and GPS devices may be employed to detect patient activity, patient location, body orientation, or torso position.

PIMD 1200 may be implemented to communicate with a patient management server or network 1234 via an appropriate communications interface or an external programmer 1230. A PIMD 1200 of the present invention may be used within the structure of an advanced patient management (APM) system. The advanced patient management system allows physicians to remotely and automatically monitor cardiac and respiratory functions, as well as other patient conditions. In one example, a PIMD 1200 implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a PIMD or patient-external medical device. It is understood that a wide variety of such devices and other implantable/external cardiac monitoring and/or stimulation device configurations are contemplated, ranging from relatively sophisticated to relatively simple designs. As such, particular PIMD/external or cardiac monitoring and/or stimulation device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
   a medical device comprising sensing circuitry;
   detection circuitry disposed in the medical device and coupled to the sensing circuitry, the detection circuitry configured to detect one or more respiratory parameters;
   a memory configured to store a baseline weight of a patient; and
   a processor coupled to the memory and the detection circuitry, the processor configured to compute a change in the one or more respiratory parameters relative to a first threshold, compute a prediction of change in patient weight based on the computed change in the one or more respiratory parameters, and generate an output signal in response to the patient weight change prediction exceeding a second threshold, the processor further configured to update the first and second thresholds in response to the change in the one or more respiratory parameters exceeding the first threshold and the patient weight change prediction exceeding the second threshold.

2. The system of claim 1, wherein the change in the one or more respiratory parameters represents a cumulative change or slope of change in the one or more respiratory parameters.

3. The system of claim 1, wherein the processor is configured to compute the patient weight change prediction by deriving coefficients based on a relationship between predicted patient weight change relative to change in the one or more respiratory parameters.

4. The system of claim 3, wherein the processor is configured to derive the coefficients from a linear regression of the patient weight change prediction relative to the change in the one or more respiratory parameters.

5. The system of claim 1, wherein the one or more respiratory parameters comprises respiration rate, and wherein the processor is configured to generate a baseline relationship between the patient weight change prediction relative to change in the respiration rate for the patient, and update the baseline relationship in response to a change in therapy delivered to the patient or a change in patient condition.

6. The system of claim 1, wherein the medical device is at least partially implantable in the patient, and the processor configured to generate the output signal comprises a processor of the at least partially implantable medical device.

7. The system of claim 1, wherein the medical device is configured for implantation in the patient, and the processor is disposed in the implantable medical device.

8. The system of claim 1, wherein the processor configured to generate the output signal comprises at least a processor of a patient-external system.

9. The system of claim 1, wherein at least the sensing circuitry comprises one or more implantable sensing components.

10. The system of claim 1, wherein the one or more respiratory parameters comprises respiration rate.

11. The system of claim 1, wherein the one or more respiratory parameters comprises an index indicative of rapid shallow breathing by the patient.

12. The system of claim 11, wherein the index is derived by computing a respiration rate and a tidal volume for each patient breath.

13. The system of claim 1, wherein the one or more respiratory parameters comprises an index indicative of dyspnea.

14. The system of claim 1, wherein the output signal comprises a signal for facilitating automated initiation, adjustment or termination of therapy delivery to the patient.

15. The system of claim 1, further comprising a user interface coupled to the processor and configured to receive the patient's baseline weight for storage in the memory.

16. The system of claim 15, further comprising a weight scale configured to communicatively coupled to the user interface and configured to provide the patient's weight.

17. The system of claim 1, wherein the processor is configured to generate an output signal indicative of the patient's congestive heart failure status based on the change in the one or more respiratory parameters and the patient weight change prediction relative to the patient's baseline weight.

18. A processor-implemented method, comprising:
detecting one or more respiratory parameters;
storing a baseline weight of a patient;
computing a change in the one or more respiration parameters relative to a first threshold;
computing a prediction of change in patient weight based on the change in the one or more respiratory parameters; and
generating an output signal in response to the patient weight change prediction exceeding a second threshold;
wherein computing the patient weight change prediction comprises deriving coefficients based on a relationship between patient weight change prediction relative to change in the one or more respiratory parameters, and each of computing the change, computing the prediction, and generating the output signal is implemented at least in part using a processor.

19. The method of claim 18, comprising updating the first and second thresholds in response to the change in the one or more respiratory parameters exceeding the first threshold and the patient weight change prediction exceeding the second threshold.

20. The method of claim 18, wherein deriving the coefficients comprises deriving the coefficients from a linear regression of patient weight change prediction relative to change in the one or more respiratory parameters.

21. The method of claim 18, wherein at least detecting the one or more respiratory parameters comprises detecting the one or more respiratory parameters from within the patient's body.

22. The method of claim 18, comprising generating an output signal indicative of the patient's congestive heart failure status based on the change in the one or more respiratory parameters and the patient weight change prediction relative to the patient's baseline weight.

23. A system, comprising:
a medical device comprising sensing circuitry;
detection circuitry disposed in the medical device and coupled to the sensing circuitry, the detection circuitry configured to detect one or more respiratory parameters;
a memory configured to store a baseline weight of a patient; and
a processor coupled to the memory and the detection circuitry, the processor configured to compute a change in the one or more respiratory parameters relative to a first threshold, compute a prediction of change in patient weight based on the computed change in the one or more respiratory parameters, and generate an output signal in response to the patient weight change prediction exceeding a second threshold, the processor further configured to compute the patient weight change prediction by deriving coefficients based on a relationship between predicted patient weight change relative to change in the one or more respiratory parameters.

24. The system of claim 23, wherein the processor is configured to derive the coefficients from a linear regression of the patient weight change prediction relative to the change in the one or more respiratory parameters.

* * * * *

UNITED STATES PATENT AND TRADEMARK OFFICE
CERTIFICATE OF CORRECTION

| | | |
|---|---|---|
| PATENT NO. | : 7,993,280 B2 | Page 1 of 1 |
| APPLICATION NO. | : 12/847645 | |
| DATED | : August 9, 2011 | |
| INVENTOR(S) | : Zhang et al. | |

It is certified that error appears in the above-identified patent and that said Letters Patent is hereby corrected as shown below:

In the Claims

Column 19, line 54, Claim 16: "coupled" should read --couple--.

Signed and Sealed this
Twenty-fifth Day of October, 2011

David J. Kappos
*Director of the United States Patent and Trademark Office*